US006323242B1

(12) United States Patent
Mueller

(10) Patent No.: US 6,323,242 B1
(45) Date of Patent: Nov. 27, 2001

(54) TREATMENT OF DISORDERS SECONDARY TO ORGANIC IMPAIRMENTS

(76) Inventor: Peter Sterling Mueller, 182 Snowden La., Princeton, NJ (US) 08540

( * ) Notice: Subject to any disclaimer, the term of this patent is extended or adjusted under 35 U.S.C. 154(b) by 0 days.

(21) Appl. No.: 09/204,124

(22) Filed: Dec. 2, 1998

(51) Int. Cl.$^7$ .......................... A61K 31/36; C07C 211/00
(52) U.S. Cl. .................................... 514/646; 564/305
(58) Field of Search ............................. 514/646; 564/305

(56) References Cited

U.S. PATENT DOCUMENTS

| | | |
|---|---|---|
| 4,443,449 | 4/1984 | Jeffery et al. . |
| 4,522,828 | 6/1985 | Jeffrey et al. . |
| 4,746,680 | 5/1988 | Jeffrey et al. ..................... 514/646 |
| 4,767,790 | 8/1988 | Jeffery et al. . |
| 4,806,570 | 2/1989 | Jeffery et al. . |
| 4,814,352 | 3/1989 | Jeffery et al. . |
| 4,816,488 | 3/1989 | Rees . |
| 4,871,774 | 10/1989 | Rees . |
| 4,929,629 | 5/1990 | Jeffrey ................................ 514/646 |
| 4,939,175 | 7/1990 | Ukai et al. ........................ 514/646 |
| 5,436,272 | 7/1995 | Scheinbaum ..................... 514/646 |
| 5,459,164 | 10/1995 | Vargas . |
| 5,589,512 | 12/1996 | Norden .............................. 514/651 |
| 5,643,916 | 7/1997 | Audia et al. . |
| 5,668,117 | 9/1997 | Shapiro . |
| 5,773,436 | 6/1998 | Müller et al. . |
| 5,780,051 | 7/1998 | Eswara et al. . |
| 5,795,880 | 8/1998 | Svec et al. . |
| 5,804,596 | 9/1998 | Majeed et al. . |
| 5,908,830 | 6/1999 | Smith et al. . |
| 5,922,341 | 7/1999 | Smith et al. . |
| 5,985,866 | 11/1999 | Müller et al. . |
| 6,075,028 | 6/2000 | Graham . |

FOREIGN PATENT DOCUMENTS

| | | | |
|---|---|---|---|
| 0 339 280 | 11/1989 | (EP) . | |
| WO 94/00047 | 1/1994 | (WO) . | |
| WO 94/00114 | 1/1994 | (WO) . | |
| WO 95/21615 | 8/1995 | (WO) . | |
| WO 98/11884 | 3/1998 | (WO) ........................ A61K/31/135 |
| WO 98/13034 | 4/1998 | (WO) ........................ A61K/31/135 |
| WO 00/10551 | 3/2000 | (WO) . | |

OTHER PUBLICATIONS

R. T. Malison et al., *Am. J. Psychiatry*, 152(9): 1359–1361 (1995).
T. M. Hyde et aL., *JAMA* 273:498–501 (1995).
S. Lipper et al., *Psychosomatics*, 27(12):849–854 (1986).
R. M. Post, *Clin. Neuropharmacol*, 2:25–42 (1977).
E. M. Ornitz et al., *Am. J. Psychiatry*, 146(7): 866–870 (1989).
*Psychiatric Annuals*, 28:424–468 (1998). (a) L. Izrayelit; (b) J. Fawcett; (c) C. A. Morgan et al.; (d) S.M. Southwick et al.; (e) J. D. Bremner; (f) D. S. Lipschitz et al.; (g) M. J. Friedman.
Devinsky et al., *Neurology*, 39:835–840 (1989).
R. W. Cowdry et al., *Arch. Gen. Psychiatry*, 45:111–119 (1988).
Yudofsky et al., *Am. J. Psychiatry*, 138:218–220 (1981).
J. Fawcett, *Psychiatric Annuals*, 27(11):725(1997).
D.M. Bear, *Cortex*, 15:357–384(1979).
W. W. Beatty and N.Monson, *Journal of the International Neurological Society*, 2:134–140(1996).
V. Goel and P. Grafman, *Neuropsychologia*, 33(5):623–642(1995).
K. Fukuda et al., *Ann. Intern Med.*, 121:953–959(1994).
A. L. Komaroff et al., *Rev. Infect. Dis.*, 13(Supp.):S8–11(1991).
A. L. Komaroff et al., *Am. J. Med.*, 101:281–290(1996).
L. J. Kirmayer et al.,*Am. J. Psychiatry*, 145:950–954(1988).
E. J. Khantzian, *Am. J. Psychiatry*. 142:1259–1264(1985).
C. Reist, et al., *Am. J. Psychiatry*, 146:513–516(1989).
A.M. Gray et al., "The Involvement of the Opioidergic System in the Antinociceptive Mechanism of Action of Antidepressant Compounds," British Journal of Pharmacology, 124, 669–674 (1998).
Friedman, Current and Future Drug Treatment for Posttraumatic Stress Disorder Patients, Psychiatric Annals, 28 (8), Aug. 1998, pp. 461–468, Aug. 1994.*

* cited by examiner

Primary Examiner—Gary Geist
Assistant Examiner—Everett White
(74) Attorney, Agent, or Firm—Hoffmann & Baron, LLP

(57) ABSTRACT

A method for treatment of neuropsychiatric symptoms or disorders emanating from primary brain or systemic impairments includes administration of an effective dose of a dopamine, serotonin, and norepinephrine reuptake inhibitor to a human in need of such treatment. The preferred reuptake inhibitor is sibutramine.

17 Claims, No Drawings

TREATMENT OF DISORDERS SECONDARY TO ORGANIC IMPAIRMENTS

The present invention relates to the pharmacological treatment of various secondary neurological, behavioral and cognitive symptoms or disorders emanating out of brain or systemic impairments, i.e, primary impairments.

The secondary symptoms and disorders include as non-limiting examples, tic and behavioral disorders including Tourette's syndrome and severe non-Tourette's motor or vocal tics; Posttraumatic Stress Disorder (PTSD); atypical attention deficit disorder with or without hyperactivity; frontal lobe defects of executive function; oscillopsia; self-mutilation; violence or rage such as in intermittent explosive disorder; asocial behavior; sexual disorders (including gender choice difficulties or hyposexuality); psychological (psychosis, violence, and confusion) and motor symptoms of Huntington's Disease (Huntington's Chorea); fatigue, exhaustion, sleep problems, and pain of Chronic Fatigue Syndrome with or without Fibromyalgia; psychosis with multiple hallucinations and delusions secondary to brain injury; and opiate narcotic addiction. It should be noted that a symptom is a single manifestation while a disorder involves more than one symptom or a cluster of symptoms.

The symptoms and disorders are secondary to the primary impairments and emanate from neurological diseases or brain lesions including Tourette's Disease, non-Tourette's tic disorders, Asperger's Syndrome, temporal lobe or other focal epilepsy, Huntington's Disease, brain tumors or cysts, systemic lupus erythematosus, viral infections and their resulting neurological injuries, and various psychological disorders such as multiple personality disorder, borderline personality, organic psychosis, and severe traumatic experiences.

BACKGROUND OF THE INVENTION

Gilles De La Tourette's syndrome is characterized by motor and vocal tics, i.e., involuntary, sudden, rapid, recurrent, nonrhythmic, stereotyped motor movement or vocalization. Some researchers hypothesize that there is a dysregulation in presynaptic dopamine function in Tourette's disorder (T.D.) and tics can be exacerbated by drugs that enhance synaptic dopamine function. R. T. Madison et al., *Am. J. Psychiatry* 152(9):1359–1361, 1995. Pharmacologic therapy has included low doses of dopamine-2 blockers and dopamine-antagonists including haloperidol, risperidone, or pimozide. T. M. Hyde et al., *JAMA* 273: 498–501, 1995. A problem with this dopamine-2 blockade is that this may often produce decreased attention, hyperactivity, dysphoria, and extrapyramidal symptoms in T.D. patients. Furthermore, if T.D. patients are treated with dopamine-2 stimulating analeptics (such as methylphenidate, dextroamphetamine, or pemoline) for their cognitive, attention, and hyperactivity problems, their motor and vocal tics are intensified. Non-Tourette's tic disorder most commonly arises out of previous analeptic treatment and persists after such treatment.

Posttraumatic Stress Disorder (PTSD) follows exposure to a traumatic experience involving actual or threatened death or injury or threat to the physical integrity of oneself or others. PTSD includes characteristic symptoms of reexperience, avoidance of stimuli associated with the trauma, and numbing of general responsiveness or hyperarousal (sleep difficulty, anger, difficulty concentrating, hypervigilance or exaggerated startle response) with clinically significant distress or impairment. It has been established that PTSD is associated with organic changes in the limbic system. It has also been suggested that a kindling model or a model of a paroxysmal disorder is applicable to PTSD (S. Liper et al., *Psychosomatics* 27 (12): 849–854, 1986). In the kindling model (R. M. Post et al, *Clin. Neuropharmacol.* 2:25–42, 1977), cumulative bioelectric changes, especially in the limbic area and secondary to repeated biochemical or psychological stress, can result in abnormal limbic or neuronal sensitization and major psychiatric disturbances. Pharmacologic therapy for stress disorders has included benzodiazepines (e.g., lorazepam, diazepam, clonazepam), beta adrenergic blockers and anti-seizure medications such as carbamazepine and valproic acid. It has been suggested that PTSD can induce a longlasting brainstem dysfunction resulting in loss of the normal inhibitory modulation of startle response, (E. M. Ornitz et al, *Am. J. Psychiatry* 146(7): 866–870, 1989) and clonidine has been used to decrease noradrenergic action and inhibit startle response. Nevertheless, no successful dramatic treatment of PTSD has been discovered for the severe, chronic cases of this crippling disorder. A number of articles describing current developments in PTSD appear in *Psychiatric Annals* 28:424–468, 1998.

Multiple Personality Disorder is a Dissociative Disorder which includes the existence within the person of two or more distinct personalities which recurrently take full control. There is an extensive inability to recall personal information. Dissociative disorders may occur as acute responses to overwhelming trauma and are common in combat or disasters. There is probably also a relationship between seizures and these disorders. Devinsky et al., *Neurology* 39:835–840, 1989.

Borderline personality disorder is characterized by tumultuous interpersonal relationships, labile mood status, and behavioral dyscontrol. Self-mutilation and violent behavior can also be seen with this disorder. Carbamazepine, an anticonvulsant with preferential action on limbic foci, produced decrease in severity of behavioral dyscontrol (R. W. Cowdry et al., *Arch. Gen. Psychiatry* 45:111–119, 1988) but not in the other multiple symptoms.

Primary attention deficit hyperactivity disorder (ADHD) is characterized by developmentally inappropriate failures of attention, hyperactivity, cognitive function, and impulsivity. The ADHD syndrome is idiopathic (no known secondary cause such as brain injury, dementia or known metabolic disease), begins at birth or soon thereafter, and usually has a strong hereditary basis.

Violence or rage (intermittent explosive disorder) can also be categorized as an impulse control disorder. There is a loss of control grossly out of proportion to any precipitating psychosocial stresses. Disabling outbursts of rage and violent behavior can be related to chronic brain syndrome associated with irreversible CNS (central nervous system) lesions. Yudofsky et al., *Am. J. Psychiatry* 138:218–220, 1981. Disorders characterized by severe episodic dyscontrol can result from brain dysfunction, e.g., resulting from a failure of modulation of electrical disturbances in the limbic system (amygdala, hippocampus, hypothalamus), temporal lobe epilepsy (TLE), brain lesions or injuries which can have neurological side effects. Other brain dysfunction disorders include motor, personality, or behavior patterns arising from, e.g., neurological impairment in the brain, TLE, viral infections, neurotransmitter disorders, amino acid imbalance, brain tumors, chromosomal abnormalities, metabolic disorders including endocrine disorders, diabetes, and genetic disorders such as disease which involves several genes, and chromosomal disorders.

Temporal lobe lesions may be brain damage produced by injury, disease, viral infection, and surgery, and can produce disturbances characterized, e.g., by seizures, which can include, e.g., motor phenomena, impairment of external awareness, depersonalization, emotional changes, behavioral disturbances, psychosis, multiple cognitive disturbances, distortions or hallucinations of any of the five senses, and autonomic disturbances (gastrointestinal, cardiac, sweating, and headache symptoms among others). The symptoms can be severe and difficult to treat. The drugs used in treatment depend on the type of seizures and have included phenytoin, carbamazepine, valproic acid, phenobarbital, primidone, felbamate, gabapentin, and lamotrigine.

Various pharmacological approaches have been taken in treating the conditions described above. For example, a number of medications such as lithium, neuroleptics, anticonvulsants, buspirone and beta blockers have been used to reduce violent behaviors as a symptom, but there are no officially labeled treatments for violent behaviors. J. Fawcett, *Psychiatric Annals* 27(11):725, 1997. But, particularly when the symptoms are very severe, the standard pharmacological approaches to alleviate the symptoms of episodic dyscontrol are often unsuccessful.

Temporal lobe epilepsy poses particular problems which can include simple partial seizures that can be manifested by motor symptoms, sensory symptoms, or psychic symptoms including impairment of consciousness, dysphasia, dysmnesia, illusions, and hallucinations. Complex partial seizures include impaired consciousness and psychic symptoms. The drugs used in treatment depend on the type of seizures and have included phenytoin, carbamazepine, valproic acid, phenobarbital, primidone, felbamate, gabapentin, and lamotrigine.

Temporal lobe epilepsy (TLE), and other organic brain disorders may be associated with various sexual impairments. See, e.g., D. M. Bear, "Temporal Lobe Epilepsy—A Syndrome of Sensory-Limbic Hyperconnection", *Cortex* 15:357–84, 1979. The most common sexual effect of organic brain problems is a loss of sexual interest and drive (hyposexuality). Less often sexual preference changes can occur and rarely fetishistic, exhibitionistic, or sadomasochistic problems occur. Some patients also develop an obsessive concern about sex and sexual performance. Treatment for these sexual problems is poor with antiepileptic or psychiatric medications but at times has been altered by unilateral temporal lobe surgery, a rather heroic procedure that many, if not most, patients are unable to undergo.

Damage to frontal lobes can also impair the executive function, that is the ability to plan, initiate, organize, carry out, monitor, and correct one's own behavior. W. W. Beatty and N. Monson, "Problem Solving By Patients With Multiple Sclerosis", *Journal of the International Neurological Society* 2:134–140, 1996; V. Goel and P. Grafman, "Are Frontal Lobes Involved With Planning Functions? Interpreting Data From the Tower of Hanoi", *Neuropsychologia* 5:623–642, 1995.

Sexual abnormalities can be associated with epilepsy or other brain diseases. These include a loss of sexual interest and drive (hyposexuality); fetishistic, exhibitionistic, or sadomasochistic problems; sexual preference changes, (homosexuality, transsexuality, or transvestism); obsessive interest in sex or sexual performance; or compulsive sexual activity. Homosexuality may become a problem for those patients who have difficulty accepting this change or who are under societal pressure. It has been long established that altered sexuality can result from various brain impairments including temporal lobe epilepsy. D. M. Bear, *Cortex* 15:357–384, 1979.

Huntington's Disease (H.D.) is a relatively rare (6/10,000 in U.S. and Europe) fatal neurological disorder of a hereditary nature. It is an autosomal chromosome 4 dominant disorder with full penetrance (50% chance of all children of being affected) which usually begins between age 35–40 years and kills the patient in about 15 years with severe behavioral and neurological impairments in this morbid period. There are no successful treatments of these behavioral or neurological disorders of H.D. Neither gamma amino butyric acid (GABA) agonists (i.e. carbamazepine or valproic acid) nor antipsychotic medications repair the behavioral or neurological problems of H.D. in any satisfactory fashion.

Fibromyalgia (FM) and Chronic Fatigue Syndrome (CFS) are similar problems of unknown cause which lead to considerable suffering and debility over 6 months or more and often for many years. The incidence is approximately 250 per 100,000 for CFS and as high as 5% of the general medical population for FM. There are no reliably successful treatments and certainly no FDA approved treatments for these two disorders. FM and CFS share in common severe fatigue, impaired concentration and memory, exercise intolerance, unrefreshing sleep, muscle and joint pain, malaise, and headaches. FM is differentiated from CFS by specific point pain spots in the muscles and CFS differs from FM by having a sore throat, tender cervical or axillary lymph nodes, variably elevated erytlirocyte sedimentation rate, occasional low grade temperature, and a variety of immunologic or neuroendocrinologic test values (none of which are consistent or indicative of any known etiologic agent) See, e.g., K. Fukuda et al., *Ann. Intern. Med.* 121:953–959, 1994; A. L. Komaroff et al., *Rev. Infect. Dis.* 13(Suppl. 1):S8–11, 1991. Both are clearly different from a depressive diagnosis. A recent study by A. L. Komaroff et al, *Am. J. Med.* 101:281–290, 1996, showed marked impairment of the CFS patients vs. patients with hypertension, acute myocardial infarction, multiple sclerosis, NIDDM, diabetes, congestive heart failure, or depression. Moreover, the degree and pattern of impairment CFS was different from that seen in depression. This is also the case in Fibromyalgia. L. J. Kirmayer et al., *Am. J. Psychiatry* 145:950–954, 1988.

Opioid or narcotic abuse or addiction, most particularly addiction to or involving the abuse of heroin, but which also may involve other opiates such as propoxyphene, meperidine, hydromorphine, codeine, levorphanol, methadone, oxycodone, morphine, hydrocodone bitartrate and other opiate derivatives, represents a major drug problem throughout the world. It probably results from at least two events: 1.) a chance or purposeful exposure of the addict or abuser to one of these opiates (either through illegal sources or medical sources) with the intake by oral, nasal, or intravenous routes, and 2.) the individual exposed may have special needs for drugs which mute pain and distress. For instance, it is an infrequent event for patients to whom narcotics are administered for medical needs to develop dependence and addiction although they may show transient tolerance during treatment or withdrawal symptoms after cessation of the treatment. The binding sites in the brain and elsewhere of these opiate drugs are similar to the sites where our own endogenous pain-relieving endorphins and enkephalins bind. It has been proposed (E. J. Khantzian,*Am. J. Psychiatry* 142:1259–1264, 1985) that those who abuse narcotics as a drug of choice for dependence abuse or addiction are those who are subject to disorganizing and threatening affects of rage and aggression, perhaps from inadequate responses of their own endogenous pain-relieving endorphins. Many of these patients do not feel relief of pain over time the way most other people do. Treatment results for this serious addiction problem are extremely poor, mainly because of the lack of any non-addicting drug that can relieve the craving for narcotics in these addicts. Methadone treatment has been used commonly but methadone is just another addictive opiate which can be given conveniently in an oral form. Nevertheless, methadone is frequently abused and sold for abuse by addicts and others. There are no FDA-approved non-narcotic treatments for the chronic abuse of opiate narcotics.

Sibutramine hydrochloride monohydrate (N,N-Dimethyl-1-[1-4-chlorophenyl cyclobutyl]-3-methylbutylamine hydrochloride monohydrate) available as MERIDIA® (Knoll Pharmaceutical Co., Mount Olive, N.J.) has been described for the treatment of obesity and depression (U.S. Pat. Nos. 4,746,680, 4,929,629 and 5,436,272), for diabetic hyperglycemia (WO 98/11884), and for hyperlipidemia (WO 98/13034). In contrast to many of the drugs mentioned above, sibutramine's mode of action is believed to include, among other things, inhibition of serotonin, norepinephrine, and dopamine reuptake. Accordingly, it intensifies all three of these brain neurotransmitters at their post-synaptic receptor sites. These results are described, e.g., in U.S. Pat. No. 4,939,175 which also discloses the use of N,N-dimethyl-1-[1-(4-chlorophenyl)cyclobutyl]-3-methylbutylamine to activate the central nervous system and thereby improve certain cerebral functions involved with memory such as senile dementia, amnestic syndrome, and learning, and to increase spontaneous movement as in Parkinson's disease. There is no suggestion, however, to treat the neuropsychiatric symptoms and disorders treated according to the invention, i.e., neurological, behavioral and cognitive symptoms, particularly symptoms refractory to previous treatments.

It is an object of the invention to provide a treatment for severe secondary symptoms and disorders which often have not been successfully treated heretofore.

SUMMARY OF THE INVENTION

The invention provides a method of treating secondary neurological, behavioral, and cognitive symptoms or disorders emanating from primary organic impairments. The term neuropsychiatric will be used herein to encompass these neurological, behavioral and cognitive symptoms or disorders.

The conditions to be treated encompass symptoms and disorders including vocal and motor tics, obsessive compulsive behavior, and cognitive and behavior disorders of Tourette's syndrome and non-Tourette's disorders; symptoms of Posttraumatic Stress Disorder (PTSD); symptoms of multiple personality disorder; symptoms of Attention Deficit Hyperactivity Disorder (ADHD) or Attention Deficit Disorder (ADD); violence or rage such as seen with an intermittent explosive disorder; adult or adolescent sexual disorder or sexual dysfunction including hyposexuality, hypersexuality, obsessive-compulsive sexual activity, gender choice problems (including homosexuality), and sexual deviations (fetishism, transvestism, pedophilia, sadomasochistic behavior, exhibitionistic behavior, and frotteurism); self mutilation including self-laceration and other self-abuse; oscillopsia; psychological, behavioral, emotional, cognitive and motor symptoms of Huntington's Disease; severe fatigue, sleep abnormalities, cognitive difficulties, and pain of fibromyalgia and chronic fatigue syndrome; severe psychoses with hallucinations and/or delusions refractory to conventional antipsychotic treatment as caused by primary impairments including trauma, brain tumors, amino acid imbalance, chromosomal abnormalities, metabolic disorders including renal failure and diabetes, and genetic disease; frontal lobe executive problems of forming appropriate plans and carrying them out in prompt fashion caused by various primary brain disorders; asocial behavior; and opiate narcotic dependency, abuse, or addiction. Patients advantageously treated have at least one of these symptoms or disorders.

The primary impairments which give rise to these symptoms include as non-limiting examples, temporal lobe epilepsy (TLE), Huntington's Disease, Tourette's Disorder, non-Tourette's Disorder, atypical attention deficit disorder with or without hyperactivity, adult or adolecent sexual disorders, Posttraumatic Stress Disorder (PTSD), multiple personality disorder, borderline personality, and organic psychosis. The primary impairments can be systemic such as systemic lupus erythematosus; brain disorders from systemic causes such as metabolic, genetic or chromosomal diseases, brain cysts, and tumors; Fibromyalgia, Chronic Fatigue Syndrome; viral infections and resulting neurological injuries.

The treatment includes administering a pharmacologically effective dose of a dopamine, serotonin and norepinephrine reuptake inhibitor, particularly sibutramine, to a human in need of such treatment. The treatment has also been shown to interrupt endorphin-opioid pathology. Patients most advantageously treated are those with severe symptoms. By severe is meant intractable symptoms which have not responded to standard medication sufficiently to control those symptoms.

DETAILED DESCRIPTION OF THE INVENTION

There are many secondary symptoms or disorders caused by or excited by various primary excitatory factors or impairments (diseases, illnesses, injuries, etc.). The primary impairments include brain impairments such as brain disease, brain lesions, and systemic impairments such as lupus erythematosus, fibromyalgia, and chronic fatigue syndrome.

It has been discovered that administration of sibutramine allows control of previously uncontrollable behavioral, cognitive, and neurological problems in patients suffering from a spectrum of neurological disorders. Clinical results show that symptoms successfully controlled include tics manifested by motor or vocal outbursts, episodic dyscontrol with anger and violence, self injury or mutilation, asocial behaviors, problems of executive (frontal lobe) function, severe posttraumatic stress disorder, panic outbursts, atypical psychoses with florid hallucinations and delusions refractory to previous treatments, the severe behavioral motor and psychotic symptoms of Huntington's Disease (HD), atypical attention deficit disorder, sexual disorders, sleep problems, fatigue, cognitive dysfunction, or pain problems of fibromyalgia or chronic fatigue syndrome, and the opiate narcotic craving in opiate addiction.

Many of the disorders and symptoms are listed in The Diagnostic and Statistical Manual of Mental Disorders (DSM-IV) of the American Psychiatric Association, Washington, D.C.

The term sibutramine as used herein means compounds of sibutramine hydrochloride monohydrate, more specifically N,N-dimethyl-1-[1-(4-chlorophenyl)cyclobutyl]-3-methylbutylamine hydrochloride preferably in its monohydrate form, and enantiomers and analogues thereof, as described in U.S. Pat. Nos. 4,746,680, 4,929,629 and 5,436,272. Sibutramine is believed to inhibit reuptake of norepinephrine, serotonin and dopamnine thereby intensifying their effects in the brain. Sibutramine is commercially available as MERIDIA®, Knoll Pharmaceutical Company, Mount Olive, N.J. Capsules are presently available with discrete dosages of 5, 10 and 15 mg for oral administration. The sibutramine is administered in a pharmaceutically active dose. The preferred dosage is about 5 mg three times a day but there is variation between patients for the best dose. It is believed that the cytochrome P450 system differs in individuals and the dose must be determined empirically in each patient. The effect of the cytochrome P450 system on metabolism of psychotropic drugs is discussed in "Intercom: The Experts Converse", published by The Journal of Clinical Psychiatry, November 1995. The lowest effective dose has been shown to be 0.25 mg daily and the highest dose has been shown to be 45 mg (15 mg 3 times daily). It is possible that higher or lower doses can be used depending upon each individual. Therefore, more flexibility in available dosage is needed. Furthermore, means of administration such as injection, rectal suppository, or transdermal patches may be utilized. Finally, a long-acting slow-release means such as oral tablet or capsule would be the preferred route in view of the rapid metabolism noted (5 hour duration of action usually) in most of the patients.

The sibutramine, sibutramine salt or derivative thereof, is administered, preferably in a pharmaceutical carrier and in a pharmaceutically effective dose, preferably about 5 mg three times a day. The dose can vary depending upon the individual, e.g., from about 0.25 mg to 45 mg or more per day.

Although the use of sibutramine has been described for the treatment of conditions such as obesity, depression, diabetic hyperglycemia, hyperlipidemia, senile dementia and related conditions, and Parkinson's disease, it has been discovered that sibutramine can be successfully used in treating other problems unrelated to these conditions. In treating other problems according to the invention, for example, rather than demonstrating an anti-obesity effect, most patients gained weight when the changes resulting from the method of the invention were taking place. For example, patients with ADD previously treated with stimulants found it easier to eat when treated with sibutramine and gained weight. Moreover, the improvements according to the invention were rapid and the symptoms were alleviated within minutes or hours of treatment. Therefore, the improvements were seen in the short term, and the improvements continued long term. In regard to depression, most of the patients treated were not clinically depressed and patients who were being treated with anti-depressants became depressed when removed from the anti-depressant medication and treated with sibutramine alone. It was generally necessary to continue anti-depressant therapy along with the sibutramine therapy.

It has been discovered that sibutramine acts as a stabilizer or normalizer of the secondary effects of various neuropsychiatric conditions. Sibutramine appears to correct multiple secondary, ancillary neurophysiological signs and symptoms of many neuropsychiatric disorders. While it is not intended to be bound by theory, this may be through a "damping" neurological effect which would restrict or mute abnormal impulses emanating from the area of pathology or injury (such as the temporal lobe) to peripheral areas (such as the hypothalamus, the amygdala, the hippocampus, other limbic structures, or motor areas). Sibutramine is therefore usually an "add-on" medication to other medications, such as antiepileptic or anti-depressant medications. It appears to be one of those very rare if not unique medicines that calms without sedating, activates without agitating, or, in sum, corrects these multiple severe neurophysiological problems toward normal. For many of the patients it also helps frontal lobe planning in executive function, thereby not only helping attention, but also intention.

Above and beyond the known effects of sibutramine on serotonin, dopamine and norepinephrine activation, there is believed to be an effect of this medication on the endorphic opiate neurotransmittor system which is evident in the patients who have been relieved of pain, rage, anger, self-mutilation and particularly addiction to heroin. Moreover, self-injury appears to activate the opioid system and the relief through sibutramine of the need to cut themselves in these patients strongly suggests endorphic involvement of some sort. It would appear that sibutramine activates endorphins or, at the very least, modifies the endorphinergic opioid systems to promote serenity and lack of pain and stress, and to reduce craving for heroin. Such a mechanism which was previously unsuspected may have also contributed to the therapeutic effects of sibutramine herein described for PTSD, asocial behavior and fibromyalgic pain which have not been helped by serotonin, dopamine and norepinephrine potentiators. This is in contradistiction to the therapeutic effects of sibutramine on ADHD, chronic fatigue, and the symptoms of Tourette's and nonTourette's diseases. Finally, a differentiation between the serotonin, dopamine and norepinephrine potentiation versus the opiate-like therapeutic effects of sibutramine may be made in terms of duration of action, whereas the serotonin, dopamine, norepinephrine agonist effects lasted in most patients for only 4–6 hours (therefore requiring tid dosage), the opiate effects appear to last all day and require only a single AM dosage.

Furthermore, for most of these disorders, at this time there are no other known nor FDA approved medications currently available. The following nonlimiting examples illustrate the invention. In the following case histories, problems (symptoms or disorders) helped included:

1. Rage, violence and self-abuse. (Case Nos. 3, 47, 54, 97, 100, and 113)
2. Organically-based sexual dysfunction (including hyposexuality, obsessive-compulsive sexual preoccupation, and gender choice problems). (Case Nos. 20, 54, 77, 99, 100, and 109)
3. Severe post-traumatic stress disorder (PTSD). (Case No.74)
4. The behavioral-emotional problems of Huntington's Disease. (Case No.113)
5. Oscillopsia associated with brain injury. (Case No.111)
6. Treatment refractory Attention Deficit Disorder (ADHD) or (ADD) with or without hyperactivity. (Case Nos. 16, 20, 41, 47, 76, 77, 78, 100 and 109)
7. Tics, concentration problems, and behavioral problems of Tourette's Disease. (Case Nos. 20 and 47and non-Tourette's Disease (Case No. 76).
8. Asocial behavior. (Case Nos.20 and 54)
9. Severe atypical and neuroleptic refractory psychoses with delusions, hallucinations, and dyscontrol. (Case No.97)
10. Enhancement of frontal lobe (executive planning) function (Case Nos. 41 and 78).
11. The fatigue, cognitive problems, sleep disorders, and pain of fibromyalgia or chronic fatigue syndrome (Case No. 141).

12. The craving for opiates in the dependent patient (case No. 165)

Some of the cases illustrate multiple problems.

EXAMPLES

1. Severe Atypical Psychosis (Problem No.9)
Sibutramine Patient No.97

A 33-year-old male patient had been treated for a severe psychosis which emanated from a motor vehicle accident with head trauma. Symptoms included multiple hallucinations (visual, auditory, smell, and touch), paranoid delusions, confusion, impaired memory, and discontinuity in awareness. He had received various a psychiatric diagnoses and had been treated without success with haloperidol, risperidone, olanzapine, trifluoperazine, buspirone, paroxetine, lorazepam, amantadine, and fluoxetine. SPECT brain scan showed multiple foci of dysfunctions in the right hemisphere indicative of right hemisphere encephalopathy (rather than a primary psychiatric disorder). Treatment with carbamazepine and quetiapine did not control his symptoms and valproic acid was also added. Finally, the patient was started on sibutramine 10 mg orally three times a day and the patient noted a marked decrease in hallucinations, confusion, paranoia, and anxiety. He continued on this treatment for seven weeks and beyond with gradual and consistent improvements.

2. Violence and Self-Laceration (Problem No. 1)
Sibutramine Patient No.3

A 49-year-woman had been treated for over eleven years for a complex partial seizure disorder with marked mood swings, frequent suicide attempts, out-of-body experiences, auditory, visual, and smell hallucinations, violent periods, and self-abuse (cutting herself). She required large doses of carbamazepine, valproic acid, gabapentin, trazodone, fenfluramine, nadolol, olanzapine, and venlafaxine to minimize her seizures (several per week) and to keep her out of psychiatric hospitals (a number of admissions), but she continuously suffered from self-abuse, rage attacks, loss of energy, and violent mood swings. She was rejected for brain surgery because of multiple foci for her seizure disorder.

She was started on sibutramine 10 mg orally every morning for her violence, self-abuse and obesity. Within less than a week, the patient gained new energy, had fewer seizures, and was no longer violent or self-abusive. Her dose of sibutramine was adjusted to 5 mg orally three times a day within the first two weeks of treatment due to a rapid wear-off of effects within 5–6 hours of administration. The patient had little weight change, actually gaining four pounds during the first month of treatment when these rapid behavioral and psychological changes were noted and therefore were clearly not related to the approved uses of sibutramine.

3. to 7. Repair of Altered Sexuality (Problem No. 2)

As discussed above, head injury temporal lobe epilepsy (TLE), and other organic brain disorders may be associated with various sexual impairments. The most common sexual effect of organic brain problems is a loss of sexual interest and drive (hyposexuality). Less often sexual preference changes can occur and rarely fetishistic, exhibitionistic, or sadomasochistic problems occur. Some patients also develop an obsessive concern about sex and sexual performance. The following case histories 3 through 7 illustrate the rapid repair of these organically based sexual problems with sibutramine.

3. Sexual Function, ADD, and Rage Outbursts (Problem Nos. 1, 2, and 6)
Sibutramine Patient No.100

A 51-year-old married man was treated for over two years for a simple partial seizure disorder of post-traumatic TLE (three automobile accidents) with severe mood swings, suicide attempts, obesity (over 300 lbs., and a body mass index of 41), memory problems, decreased organization, concentration problems, decreased sexual drive, and rage attacks. SPECT and EEG studies showed diffuse abnormalities in both frontal and parietal lobes. Previous treatment for his mood swings with lithium carbonate was unsuccessful and made his obesity worse. Treatment for his cognitive problems with bupropion, imipramine, nortriptyline, methylphenidate, and dextroamphetamine were unsuccessful.

Treated with carbamazepine helped with his mood swings but not with his anger, sexual, or cognitive problems. Treatment with phenteramine 15 mg twice a day helped him lose a small amount of weight but did not affect his other problems. Treatment with magnesium pemoline, lamotrigine, desipramine, selegiline, olanzapine, valproic acid, donepezil, thyroxine, fenfluramine and long-acting amphetamine salts were also not helpful. A trial of sildenafil (Viagra) did not help his sexual libido.

The patient was started on sibutramine 10 mg twice a day and he soon noted an increase in his sexual drive and interest in distinct contrast to his lack of response to sildenafil. He was able to concentrate better and had fewer and less severe anger outbursts.

4. Sexual Function and ADD (Problem Nos. 2 and 6)
Sibutramine Patient No.109

A 56-year-old married man had been treated for a year and a half for a simple partial seizure disorder of TLE with visual illusions, mood swings, anger attacks, and a loss of sexual interest and drive. He also had a separate problem with a prostatitis, urethritis, and prostatic calculi which further impaired his sexual life. Valproic acid helped his anger attacks but interfered with his concentration considerably and did not help his sexual problems. Other unsuccessful treatments included magnesium pemoline, lamotrigine, propranolol, and donepezil. Prostatic surgery with the removal of calculi helped his sexual performance marginally but not his sexual interest. Other unsuccessful treatments included yohimbine, testosterone patches, and sildenafil, which only increased sexual function but not libido. He was started on sibutramine 5 mg three times daily and immediately noted a new-found interest and ability to engage in sex. Finally, he no longer had the concentration and fatigue problems he had suffered from with the continuing valproic acid treatment.

5. Tourette's Tics, Asocial Behavior, and Relief of Hyposexuality (Problem Nos. 2, 6, 7, and 8)
Sibutramine Patient No. 20

A boy was diagnosed at age 4 with ADHD (Attention Deficit Hyperactivity Disorder) and at age 6 ½ years with Tourette's Disease. He had developmental delays as well as severe learning disabilities. He had violent behavior, dangerous impulsive behavior (jumping out of a second story window), marked social inappropriateness, and asocial behaviors of odd communication. He has been on medications since the age of four and at the time of this writing is now 16.

He was extremely difficult to medicate because any medication which helped the ADHD worsened his Tourette's Disease symptoms. Likewise, any effective Tourette's medication worsened his ADHD or his cognitive function. He had been given numerous medications over the years and none could improve his function without causing severe side effects or worsening other symptoms. In fact, he was hospitalized twice (103 days and 35 days) and in both cases it was reported that it was next to impossible to medicate him correctly. He was completely dysfunctional without medications or on the wrong medications and nearly required placement out of the home in an institution. Medications that were tried without success included: haloperidol, pimozide, fluphenazine, olanzapine, fenfluramine, dextrofenfluramine, carbamazepine, valproic acid, clomipramine, methylphenidate, magnesium pemoline, fluvoxamine, tacrine, donepezil, dextroamphetamine, felbamate, gabapentin, lamotrigine and seligiline. Clozapine was helpful in controlling his behavior and helped somewhat with his verbal tics but produced sedation, worse ADHD, and cognitive problems. (IQ fell 30 points). It also did not help his social behavior.

He was started on sibutramine (5 mg three times a day) and improvement was shown in many ways. First, the motor and vocal tics associated with Tourette's Disease were decreased as well as the obsessive compulsive component. Secondly, his ADHD improved; he became calmer and his thought processes clearer (decreased racing thoughts). Thirdly, his communication and social skills improved. He began dating girls for the first time. Prior to this he had no interest in sexual matters. He began attending regular mainstream school. Finally, many of the inappropriate behaviors ceased. These improvements included looking at people when he talked, directed rather than circumstantial speech, and appropriate social behavior which permitted him to be popular with his peer group. Prior to sibutramine treatment he had not begun to cope with the problems of adolescence but had remained sexually undifferentiated and socially remote.

6. Sexual Obsessive-Compulsive Behavior, ADD and Executive Function (Problem Nos. 2, 6 and 10)

Sibutramine Patient No. 77

A 47-year-old married man had been treated for TLE simple partial seizure disorder for about six months. Among his complaints were inattention, poor organization, mood swings, sexual preoccupation, compulsive sexual behavior, visual illusions, and discontinuities in awareness. He had a past history of alcoholism but had been abstinent for ten years. He had been treated for a number of "psychiatric" disorders including "schizophrenia," "depression," "mania," and "ADD." Past unsuccessful medicines had included haloperidol, dextroamphetamine, buproprion, and valproic acid.

Treatment with carbamazepine corrected the mood swings, breaks in awareness, and visual illusions, but not his lack of concentration, his disorganization, nor his sexual preoccupations and compulsive activity. Trials of added methylphenidate, long-acting amphetamine salts, and magnesium pemoline were also unsuccessful in this regard. He was started on sibutramine 10 mg every morning by mouth and after a month the dose was increased to 5 mg three times a day by mouth because the duration of effects of each dose was about five hours. On this medication, he could concentrate, organize, and no longer had the sexual obsessive-compulsive problems. Despite this decreased sexual activity, he has a more enjoyable sexual life with his wife with sibutramine treatment.

7. Sexual Gender Choice Change: Homosexuality (Problem No. 2)

Sibutramine Patient No. 99

A 20-year-old young man had been treated for TLE with partial seizures, disorganization, and suicidal behavior (particularly when abandoned by a male lover). He had a history of head injury at age 1-½ years when he fell off a dresser while having a diaper change. He had been seen by multiple psychiatrists since age 13 years for depression that was refractory to imipramine, sertraline, lithium carbonate, fluoxetine, methylphenidate, gabapentin, donepezil, and olanzapine. The patient's impulsive behaviors, mood swings, and epileptic symptoms were relieved by carbamazepine.

His sexual history was significant in that he was completely asexual with no interest in either males or females until age 14 years when he began autoerogenous activity with thoughts of men. At age 16 years, he began homosexual activity. The sexual behavior continued for the 1-½ years he was treated with carbamazepine. A marked change occurred after he was started on sibutramine 10 mg every morning. He first noted an increased interest in sex generally, but for the first time this interest included females as well as males. His interest in women became heightened with a differentiation between "attractive" and "non-attractive" girls, something he had not even considered previously. He became interested in female anatomy for the first time. A major issue became his complete lack of knowledge of dating and sexual conventions with girls. As a result, he gave up sexual activity (but not interest) until he could acquire the necessary social skills with girls. Most recently he had intercourse with a woman. His present dose of sibutramine is 5 mg three times a day.

8. Tourette's Disease Tics, Violence, and ADHD (Problem Nos. 1, 6, and 7)

Sibutramine Patient No. 47

An 18-year-old male was treated for Tourette's Disease with vocal and motor tics, attention deficit disorder, and episodic anger and violence, for over six years. Treatment had included phenytoin, phenobarbital, clonidine, carbamazepine, fenfluramine, magnesium penoline, valproic acid, hydroxyzine, methylphenidate, bromocriptine, clomipramine, desipramine, selegiline, propranolol, clozapine, felbamate, tacrine, gabapentin, risperidone, lamotrigine, olanzapine, donepezil, and quetiapine without any good results. The medicines that helped the tics made his violent outbursts and cognitive problems worse and vice versa. The one exception was donepezil 5 mg bid p.o. which helped his cognitive problems without aggravating his tics or his outbursts; yet donepezil did not relieve the outbursts nor the tics.

The patient was started on sibutramine 10 mg every morning. This rapidly relieved his tics, his aggressive outbursts, and helped his concentration. The donepezil was continued. The effects of the sibutramine wore off quickly after noon with a rapid return of all symptoms. The dose of sibutramine was readjusted to 10 mg three times daily and he has continued on this medication to date with the loss of verbal and motor tics, violence, and concentration problems.

9. Non-Tourette's Tics, Obsessive-Compulsive Rituals, and Attention Deficit Hyperactive Disorder (ADHD). (Problem Nos. 6, 7)

Sibutramine Case #76

An 11-year-old boy had been treated since the age of five years for attention deficit disorder with hyperactivity. He had a difficult birth in that his mother suffered from disseminated intravascular coagulation (presumably secondary to amniotic infusion) with kidney, cardiac, and pulmonary failure. The patient himself had pulmonary and cardiac arrest at birth but was restored back to life by resuscitation and artificial life support. His development was normal except for his hyperactivity, attention deficit, and impulsivity (from which his older brother also suffered).

He was initially treated successfully with methylphenidate until age eight years when premoline was added because of the rapid wear-off from the effects of methylphenidate. Lamotrigine was added at age nine years in an attempt to help his cognitive problems without success. At age 10 years, the patient developed multiple obsessive-compulsive (OCD) symptoms of trichotillomania and lip-licking, and fluvoxamine was added. SPECT scan was negative as was his MRI. The methylphenidate was discontinued and he was treated with amphetamine salts. Although the amphetamine and fluvoxamine helped his hyperactivity and OCD symptoms in part, he went on to develop multiple vocal and motor tics. Carbamazepine, donepezil, and ropinirole were unsuccessful. Finally, sibutramine was started at 5 mg tid. This stopped both the tics and the OCD symptoms, but only for a few hours. When the sibutramine dose was increased to 10 mg tid, he was free of symptoms throughout the day. Sleep and appetite were not affected. Furthermore, his concentration at school was better than with any of the analeptics (dextroamphetamine, methylphenidate, or pemoline) which were all discontinued. Finally, if he misses a single dose of sibutramine, the vocal and motor tics return immediately; this clearly identified the duration of action of sibutramine and was typical for most of the 170 patients treated to date.

10. Asocial Behavior, Violence, and Hyposexuality (Problem Nos. 1, 2, and 8)

Sibutramine Patient No. 54

A 31-year-old man had a life-long history of asocial behavior, violence, and mental retardation. His parents noted that he had been relatively normal until age 3 ½ when he became asocial and withdrawn and had problems with eye/hand coordination. He went on to become episodically violent. He also developed limited speech and inappropriate communication with no eye contact and lack of affect with others. He had been given multiple medications since the age of 5 years including methylphenidate, thioridazine, chloral hydrate, haloperidol, carbamazepine, nadolol, fenfluramine, propranolol, olanzapine, and quetiapine without any changes in his speech or mode of communication. The carbamazepine, high-dose propranolol, and fenfluramine combination was successful in curbing his violence but not his asocial behavior or hyposexuality. In the late fall of 1997 fenfluramine was removed from the market and the patient became episodically violent again.

In the spring of 1998 the patient was tried on sibutramine 10 mg daily and he again became calm and manageable. The dose was then changed to 5 mg tid and other changes became noticeable. These included a decrease in repetitive speech, hissing, and compulsive acts, an increase in social activity and sexual interest, and increased speech generally. Furthermore, for the first time he began to look directly and intently at the person he was talking to and made sense in his speech and oriented to the situations around him. Finally, he now was accepting change without upset for the first time.

11. Severe Post-Traumatic Stress Reaction (Problem No.3)

Sibutramine Patient No. 74

A married 53-year-old woman was seen for a very severe post-traumatic stress disorder (PTSD) which stemmed from her witnessing the murder of her employer and the suicide of the murderer by pistol shots close to her ear. The brain single photo emission computed tomography (SPECT) scan was abnormal with decreased left frontal lobe perfusion. The patient had psychotic decompensation when confronted with pistol shot-like sounds such as backfires, shots from TV or movies, and particularly thunder. During the first thunderstorm after the trauma she described rain coming down the color of blood, and she ended up curled up in a fetal position in a corner of the room with her hands over her ears in a grossly psychotic state. Treatment with carbamazepine, phenytoin, various benzodiazepines, valproic acid, various antipsychotics (including clozapine), buspirone, oxcarbazepine, various antidepressants, dextroamphetamine, pemoline, methylphenidate, and fenfluramine were all unsuccessful in preventing her severe PTSD symptoms and particularly the reactions to thunder. She frequently was suicidal and was hospitalized once for these severe problems.

The patient was started on sibutramine 10 mg in the morning and was seen two days after a very severe thunderstorm with the threat of tornadoes. The patient reported she stayed up four hours of that night watching for tornadoes, completely oblivious of her former psychotic fear of thunder.

After one and a half months sibutramine was stopped due to problems of dosage due to her deficiency in P-450 cytochrome system enzymes. Even one-half of the smallest capsule (5 mg) was too much and produced drowsiness, sugar craving, and weight gain. She also had not had any PTSD symptoms in many weeks and felt she might be over the disorder. Unfortunately, she immediately noted a rapid return of the fear of thunder, sound and light sensitivity, exaggerated startle reflex, headaches, and nightmares of life and death situations. She had to wear ear plugs and be sedated for the psychoses caused by thunderstorms or even the threat of such. Within one and a half months of the cessation of the sibutramine, the patient was returned to sibutramine but at a much lower dosage (less than 1 mg once a day). This provided relief again from her PTSD symptoms but without the sedation she had noted before with higher doses of sibutramine. Finally, this patient was taken off of fluoxetine 20 mg when sibutramine treatment was initiated. She became severely depressed despite the relief from PTSD. When the fluoxetine was reinstated, the depression and PTSD were relieved. Therefore, the effect of sibutramine on PTSD was different from any antidepressant action.

12. Huntington's Disease (Problem No. 4)

Sibutramine Patient No.113

A 39-year-old single woman had been treated for an organic behavioral disorder with mood swings, violence, concentration problems, and psychosis for over eleven years. She had been managed well and worked full-time with great success with carbamazepine, gabapentin, and fluoxetine, but she then developed staggering gait, confusion, disorganization, rage outbursts, and severe hopelessness with suicidal impulses that no longer responded to the previous medications. She was then started on sibutramine 5 mg three times a day and within 20 minutes of the first capsule she noted complete relief of the cognitive, emotional, and behavioral problems but not with the ataxic gait. These effects lasted only five hours and required at least three times a day dosage. A dosage of 5 mg at 5:30 AM and 10:30 AM and 10 mg at 3:30 PM permitted her relief until bedtime at 10:30 PM. Gradually she noted improvements in her ataxic gait and was able to continue her responsible work as a boat captain without staggering or falling. Her dose was adjusted to 10 mg tid po due to rapid wear-off of the smaller 5 mg doses. A review of her family history revealed that the patients uncle and father had H.D. and her younger brother also has the behavior and emotional complaints that the patient had prior to the worsening of the initial symptoms (without the ataxic neurological symptoms).

13. Intracerebral Porencephalic Cyst With Oscillopsia (Problem No. 5)

Sibutramine Patient No. 111

A 58-year-old man suffered a severe head injury in 1976 with a fractured skull, coma, and an intracerebral (porencephalic) cyst caused by the traumatic blockage of his cerebral spinal fluid in his brain. This cyst was repaired surgically with a brain ventricular—jugular vein shunt. This had permitted him to work continuously with concomitant treatment with carbamazepine, valproic acid, and dextroamphetamine until early 1998 when he began to suffer severe attacks of bizarrely altered vision, dizziness, ataxia, and confusion. The attacks progressed to several times per week, lasting 4–24 hours in duration. Examination revealed he was suffering from oscillopsia produced by the rapid oscillation of his eyes produced by irritation from his injury and his shunt. There is no known treatment for these attacks and he was therefore unable to drive or work safely. He was placed on total disability. He was started on 10 mg of sibutramine as needed for these oscillopsia attacks. When this appeared to help, his dose of sibutramine was increased to 5 mg three times daily. In the next four weeks he had only one such attack, and this began early in the morning prior to his initial dose of sibutramine. After 2 months at the 5 mg tid dosage, the patient again noted a recurrence of oscillopsia on a 2–3 times weekly basis. His dosage of sibutramine was increased to 10 mg tid and this was followed by an absence of attacks.

14. Severe ADHD Refractory to All Other Medications with Executive (Frontal Lobe) Problems (Problem Nos. 6 and 10)

Sibutramine Patient No. 41

A 25-year-old male was seen first for a life-long history of severe hyperactivity, distractibility, disorganization, poor memory of studied material, very poor concentration, and school failure despite a high IQ. There was no known history of head injury, other neurological disease, nor metabolic disease. He had had multiple trials (both singly and in combination and in a wide range of doses) of methylphenidate, magnesium pemoline, dextroamphetamine, venlafaxine, valproic acid, carbamazepine, lamotrigine, nefazodone, lithium carbonate, fluoxetine, imipramine, nortriptyline, buproprion, and donepezil. He was started on sibutramine, finally reaching a dose of 15 mg three times a day (due to his rapid catabolism of this medicine with a maximum duration of a single dose effect of only 4–5 hours). This was the first medication to calm him and permit careful, quiet concentration and retention of information. He now plans graduate school for the first time with confidence. The only complaints relate to being "too calm" with a loss of the exciting high-risk behavior of the past. He also noted for the first time a marked improvement in his ability to form appropriate, organized plans and execute them promptly without procrastination or distraction.

15. ADHD Refractory to Other Treatments (Problem No. 6)

Sibutramine Patient No. 16

A 46-year-old married woman with a lifelong history of ADHD was treated for four years with multiple medications including methylphenidate, magnesium pemoline, dextroamphetamine, and long-acting amphetamine salts without success and negative side effects. The amphetamines made her nervous, jittery, and unable to sleep. The methylphenidate and magnesium pemoline, on the other hand, made her sleepy. These medications did not calm her hyperactivity without sedating her. She was started on sibutramine 10 mg every morning by mouth. Immediately she noted a calming and an alerting effect not seen with the dopamine agonist analeptics. After the first month, her dose was changed to 5 mg three times daily due to a five hour duration of effects. She has continued on the medication to date (over six months) as did her daughter who also failed to respond to all of the various analeptic dopaminergic drugs used for ADHD.

16. Enhancement in Frontal Lobe Executive Function, ADHD, and Hyposexuality (Problems Nos. 2, 6, and 10)

Sibutrarnine Patient No. 78

A 65-year-old man with a lifelong history of ADHD had been treated for eight years with multiple medications. Initially his attention problems responded to methylphenidate but then required the addition of pemoline. On the other hand, his work continued to suffer due to difficulties making decisions.

Trials of adding lamotrigine, donepezil, fluoxetine, or selegiline were unsuccessful. He was then started on sibutramine 10 mg. bid p.o. and noted immediate repair of concentration, and particularly his ability to plan and carry out these plans effectively for the first time in many years. Due to dry mouth and some insomnia his dose of sibutramine was decreased to 5 mg bid and the pemoline and methylphenidate were discontinued without a loss of efficacy.

In 1997 the patient had a radical prostatectomy for adenocarcinoma of the prostate. This resulted in a lack of sexual drive and erectile dysfunction. Treatment with sildenafil helped correct the mechanical dysfunction but not the libido. With sibutramine this problem of sexual drive was repaired for the first time since his prostate surgery.

17. Fibromyalgia—Chronic Fatigue Syndrome (Problem No. 11)

As discussed above, both FM and CFS share in common severe fatigue, impaired concentration and memory, exercise intolerance, unrefreshing sleep, muscle and joint pain, malaise, and headaches. FM is differentiated from CFS by specific point pain spots in the muscles and CFS differs from FM by having a sore throat, tender cervical or axillary lymph nodes, variably elevated erytlirocyte sedimentation rate, occasional low grade temperature, and a variety of immunologic or neuroendocrinologic test values.

Sibutramine Case #141

A 52-year-old married woman had a 10 year history of fibromyalgia with multiple areas of point tenderness in her muscles, severe fatigue, marked exercise intolerance, malaise, poor concentration and memory, weight gain, headaches, and poor and unrefreshing sleep. She was tried unsuccessfully on multiple medications including most of the non-steroid antiinflammatory disease drugs and most recently nabumetone, tramadol, and oxaprozin. The patient was started on sibutramine 5 mg tid p.o.

Within 2 hours of the first 5 mg capsule the patient noted that her fatigue diminished and her energy increased substantially. She was able to eliminate her multiple rest periods and naps and able to walk up 2 levels of steps without effort as compared to her previous total exhaustion. She reported that "simple tasks became easy instead of monumentally strenuous." Despite difficulty in getting to sleep that first night after sibutramine, she woke up feeling "human" and was able to cope with the various demands of her life without fatigue or need for rest periods. She also became alert and able to concentrate. She did note that her pain points were still tender but that the burning sensation at these points had abated within 4 days. She has not have sleep problems since the first 2 days on sibutramine.

18. Relief of Heroin Craving and Abuse (Problem No. 12)

Sibutramine Patient No.165

A 19 year old single woman was introduced to heroin by snorting at age 18 years when she was particularly stressed with the anger and pain of losing a boyfriend.

She had always had difficulty recovering from pain, anger and loss but the heroin rapidly made her feel "normal". She quickly moved to the intravenous route and reached a maximum intake of 5 bags per day (approximately $100/day in cost) for the next 6 months when she was discovered to have charged large amounts on her charge cards. She was then hospitalized in a drug detoxification hospital for three weeks but soon relapsed after discharge. After her second round of treatment she was referred to the care of a psychiatrist (the inventor herein). The patient described constant, unrelenting cravings for heroin and expressed that it would be "next to impossible" to remain free of the drug for any length of time. She was started on sibutramine 5 mg tid po with no relief from her anger and hurt nor from her narcotic craving. Out of desperation, the dose was increased to 15 mg in the AM and within an hour she noted a marked change. She now felt a complete relief for the first time since her first exposure to heroin a year before. She now felt the "normal" feeling that heroin had given her and no longer noted any anger, hurt or distress. Furthermore, this effect was extended for the whole day without the rapid wearoff and tolerance that heroin had produced.

Her side effects were a dry mouth and a craving for food. She gained 15 pounds the first 2 weeks on the 15 mg of sibutramine in the morning. This was partially relieved by adding a 5 mg dose of sibutramine in the afternoon. This effect on the heroin craving and hurt is therefore clearly separate from the FDA-approved anorexic effect of sibutramine. Finally, she has had none of the negative "nodding out" side effects with sibutramine that she noted with heroin. She is now working at two jobs to pay her back debts.

I claim:

1. A method for treatment of vocal and motor tics, obsessive compulsive behavior, cognitive disorders or behavioral disorders of Tourette's Syndrome and non-Tourette's disorder comprising administering a pharmaceutically effective amount of sibutramine, sibutramine salts or derivatives thereof to a human in need of such treatment.

2. A method for treatment of symptoms of Posttraumatic Stress Disorder comprising administering a pharmaceutically effective amount of sibutramine, sibutramine salts or derivatives thereof to a human in need of such treatment.

3. A method for treatment of symptoms of multiple personality disorder comprising administering a pharmaceutically effective amount of sibutramine, sibutramine salts or derivatives thereof to a human in need of such treatment.

4. A method for treatment of rage, violence and intermittent explosive disorder comprising administering a pharmaceutically effective amount of sibutramine, sibutramine salts or derivatives thereof to a human in need of such treatment.

5. A method for treatment of self-mutilation comprising administering a pharmaceutically effective amount of sibutramine, sibutramine salts or derivatives thereof to a human in need of such treatment.

6. A method for treatment of oscillopsia comprising administering a pharmaceutically effective amount of sibutramine, sibutramine salts or derivatives thereof to a human in need of such treatment.

7. A method for treatment of fatigue, pain, cognitive problems or sleep problems of fibromyalgia or chronic fatigue syndrome comprising administering a pharmaceutically effective amount of sibutramine, sibutramine salts or derivatives thereof to a human in need of such treatment.

8. A method for treatment of behavioral, emotional, cognitive or motor problems of Huntington's Disease comprising administering a pharmaceutically effective amount of sibutramine, sibutramine salts or derivatives thereof to a human in need of such treatment.

9. A method for treatment of executive (frontal lobe) function comprising administering a pharmaceutically effective amount of sibutramine, sibutramine salts or derivatives thereof to a human in need of such treatment.

10. A method for treatment of symptoms or disorders of Attention Deficit Hyperactivity Disorder (ADHD) and Attention Deficit Disorder (ADD) comprising administering a pharmaceutically effective amount of sibutramine, sibutramine salts or derivatives thereof to a human in need of such treatment.

11. A method for treatment of symptoms of asocial behavior comprising administering a pharmaceutically effective amount of sibutramine, sibutramine salts or derivatives thereof to a human in need of such treatment.

12. A method for treatment of hallucinations, delusions and cognitive dysfunction of psychosis following brain insult comprising administering a pharmaceutically effective amount of sibutramine, sibutramine salts or derivatives thereof to a human in need of such treatment.

13. A method for treatment of opiate narcotic abuse, dependency or addiction comprising administering a pharmaceutically effective amount of sibutramine, sibutramine salts or derivatives thereof to a human in need of such treatment.

14. A method for treatment of claims 1, 2, 3, 4, 5, 6, 7, 8, 9, 10, 11, 12 or 13 wherein the pharmaceutically effective amount comprises about 0.25 mg to about 45 mg per day.

15. The method for treatment of claim 14 wherein the treatment interrupts endorphin-opiod pathology.

16. The method for treatment of claims 1, 2, 3, 4, 5, 6, 7, 8, 9, 10, 11, 12 or 13 further comprising delivering said pharmaceutically acceptable amount in a controlled or substained release form.

17. The method for treatment of claims 1, 2, 3, 4, 5, 6, 7, 8, 9, 10, 11, 12 or 13 further including an antiepileptic or anti-depressant medication.

* * * * *

UNITED STATES PATENT AND TRADEMARK OFFICE
CERTIFICATE OF CORRECTION

PATENT NO.    : 6,323,242 B1
DATED         : November 27, 2001
INVENTOR(S)   : Peter Sterling Mueller It is certified that error appears in the above-identified patent and that said Letters Patent is hereby corrected as shown below:

Column 1,
Line 39, reads "nonrhythrnic" should read -- nonrhythmic --.
Lines 43-44, reads "Madison" should read -- Malison --.

Column 4,
Line 27, reads "erytlirocyte" should read -- erythrocyte --.

Column 6,
Line 14, reads "adolecent" should read -- adolescent --.

Column 7,
Line 3, reads "dopamnine" should read -- dopamine --.

Column 8,
Line 25, reads "contradistiction" should read -- contradistinction or contradiction --.

Column 9,
Line 13, reads "various a psychiatric" should read -- various psychiatric --.

Column 14,
Line 64, reads "patients" should read -- patient's --.

Column 16,
Line 13, reads "sibutrarnine" should read -- subutramine --.
Line 44, reads "erytlirocyte" should read -- erythrocyte --.

UNITED STATES PATENT AND TRADEMARK OFFICE
CERTIFICATE OF CORRECTION

PATENT NO. : 6,323,242 B1
DATED : November 27, 2001
INVENTOR(S) : Peter Sterling Mueller It is certified that error appears in the above-identified patent and that said Letters Patent is hereby corrected as shown below:

Column 17,
Line 2, reads "not have ..." should read -- not had ... --.

Signed and Sealed this

Twentieth Day of August, 2002

Attest:

JAMES E. ROGAN
Attesting Officer        Director of the United States Patent and Trademark Office